(12) United States Patent
Iliffe-Moon (10) Patent No.: US 11,287,877 B2
(45) Date of Patent: Mar. 29, 2022

(54) SYSTEM AND METHOD FOR APPLYING ENTRAINMENT AND BIOFEEDBACK TECHNIQUES TO A USER

(71) Applicant: Bayerische Motoren Werke Aktiengesellschaft, Munich (DE)

(72) Inventor: Etienne Iliffe-Moon, Menlo Park, CA (US)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 0 days.

(21) Appl. No.: 16/882,607

(22) Filed: May 25, 2020

(65) Prior Publication Data

US 2021/0365105 A1 Nov. 25, 2021

(51) Int. Cl.
*G06F 3/01* (2006.01)
*H04N 9/31* (2006.01)

(52) U.S. Cl.
CPC .............. *G06F 3/011* (2013.01); *G06F 3/017* (2013.01); *H04N 9/31* (2013.01); *G06F 3/016* (2013.01)

(58) Field of Classification Search
CPC ............ G06F 3/011; G06F 3/017; H04N 9/31
USPC ........................................................ 345/156
See application file for complete search history.

(56) References Cited

U.S. PATENT DOCUMENTS

| | | | |
|---|---|---|---|
| 9,272,118 B1 * | 3/2016 | Acton | A61M 21/00 |
| 9,968,756 B2 | 5/2018 | Tsai et al. | |
| 10,632,278 B2 | 4/2020 | Kirszenblat et al. | |
| 2003/0199945 A1 | 10/2003 | Ciulla | |
| 2007/0100214 A1 * | 5/2007 | Steinert | A61H 1/00 600/300 |
| 2011/0298706 A1 * | 12/2011 | Mann | H04W 4/02 345/157 |
| 2014/0154647 A1 * | 6/2014 | Nolen | F41A 33/00 434/19 |
| 2014/0256511 A1 * | 9/2014 | Smith | G10H 1/42 482/8 |
| 2016/0346501 A1 | 12/2016 | Hooper et al. | |
| 2017/0080320 A1 * | 3/2017 | Smith | G16H 40/67 |
| 2019/0134396 A1 * | 5/2019 | Toth | A61N 1/08 |
| 2019/0151751 A1 * | 5/2019 | Steadman | A63F 13/211 |
| 2020/0152312 A1 * | 5/2020 | Connor | G06K 9/00335 |

FOREIGN PATENT DOCUMENTS

KR    20160087941    7/2016

* cited by examiner

*Primary Examiner* — Albert K Wong (74) *Attorney, Agent, or Firm* — 2SPL Patent Attorneys PartG mbB; Kieran O'Leary (57) ABSTRACT

Embodiments generally relate to a system and a machine-readable medium for providing an entrainment experience to a user. The system comprising an experience system in communication with one or more human sensory inputs and an entraining rhythm generation unit. The experience system configured to receive entraining rhythm information from the entraining rhythm generation unit, determine the entrainment experience based on the entraining rhythm information, and provide the entrainment experience to the user via the one or more human sensory inputs.

20 Claims, 5 Drawing Sheets

SYSTEM AND METHOD FOR APPLYING ENTRAINMENT AND BIOFEEDBACK TECHNIQUES TO A USER

FIELD

Examples relate to a system, a method, and a machine-readable medium for providing an entrainment experience to a user. In particular, examples relate to a system for creating an entrainment experience based on a biorhythm and providing that experience to the user.

BACKGROUND

The human body has a multitude of senses. Leveraging these senses, particularly in an immersive experience, can cause both physiological and psychological effects. Orchestrating multiple sensory inputs or modalities may create new experiences or generate more powerful perceptual experiences. It can also subconsciously affect a person's biorhythm.

Many industries, including the automotive industry, seek to incorporate an immersive sensory experience into their products. An immersive sensory experience that relates the human body and spatial surroundings into a flowing dynamic experience may influence a person's emotion and mood, biorhythms, awareness, enjoyment of a product. Hence, there may be a desire for an improved system that can provide a biofeedback or entrainment experience to a user.

SUMMARY

Embodiments relate to a system for providing a biofeedback or entrainment experience to a user. The system comprises an experience system in communication with one or more human sensory inputs and an entraining rhythm generation unit. The experience system is configured to: receive entraining rhythm information from the entraining rhythm generation unit, determine the entrainment experience based on the entraining rhythm information, and provide the entrainment experience to the user via the one or more human sensory inputs.

In biology, entrainment is the synchronization of an organism to an external perceived rhythm. This phenomenon occurs in all humans and some documented examples of animals. A common example of entrainment occurs in humanity when an individual taps their foot in response to a musical or dance rhythm. An entrainment experience encourages this synchronization by immersing an individual in biofeedback that reinforces in the mind of the individual the perceived rhythm.

Biofeedback can be measured or taken from an individual, it can be generated artificially, or it can be some hybrid or combination of the two. Generating altered biofeedback and then presenting it to a user using an entrainment experience may be useful for promoting positive changes within the user's body. For example, measuring a respiration rate, generating a progressively slower respiration rate, and then exposing the user to an entrainment experience may cause the user to adapt their actual respiration rate to be in synchronization with the lower, beneficial respiration rate of the entrainment experience. An entrainment experience with immersive biofeedback can create an effect similar to the sense of "body ownership," "out-of-body," or "body transfer" experiences. These occur when a user experiences a connection to an object or another being that is akin to the connection they have with their body. A common example of body ownership is the rubber hand illusion. This occurs when one watches a rubber hand being stroked, while one's unseen hand is synchronously stroked, may cause the rubber hand to be attributed to one's body, to feel like it's their hand. The relationship between one's body and external object or people can be strengthened through the use of projection. For example, projecting (such as through the use of a video media projector) a representation of a human subject's heart rate onto a fake hand or arm reinforced the rubber-hand illusion and the perception of body ownership or ownership of the fake hand (see Keisuke Suzuki et al., *Multisensory Integration Across Exteroceptive and Interoceptive Domains Modulates Self-Experience in the Rubber-Hand Illusion,* 51 Neuropsychologia 2909-2917 (November 2013)).

Using biofeedback and entrainment can lead to deeper immersion in an experience, whether that experience is purely physical, digital, or somewhere in between, such as in a virtual experience. Creating the body ownership effect—either through biofeedback, entrainment, or both—deepens the immersion in an experience and gibes the user the perception that the experience is one with themselves.

Additionally, body ownership could also include increasing a subject's awareness or connection to hidden traits of their body. Such as physical features like their internal organs. For instance, by recording a real-time infrared video of a patient's limb (e.g. arm) and projecting back a visible graphic representation of the patient's veins a patient may become more aware and connected to their blood flow throughout their body.

Body ownership can also extend into surfacing mental traits from the subconscious to the conscious. For example, studies have shown that a person's senses can be effected through the use of immersive light experiences, including altering a subject's perception of time by bathing people in light of a specific color. Also, a subject's mood may be affected through colored ambient illumination. Additionally, the use of light may also affect one's proprioception, meaning their perception or awareness of the position and movement of the body. Proprioception requires some degree of body motion to calibrate body position awareness. Therefore a person's proprioception can be altered through immersive light experiences that affect a person's awareness of their motion.

The experience system may be in communication with one or more human sensory outputs. The experience system further configured to receive feedback information from one or more human sensory outputs and provide the feedback information to the entraining rhythm generation unit.

The reinforcement of these experiences is more successful and memorable when they are multi-sensory. A flowing, dynamic, multi-sensory, immersive experience relating to a user's body and their spatial surroundings may use body ownership effect to reinforce objectives such as influencing emotion and mood, biorhythm entrainment, entertainment, and artistic performance.

The one or more human sensory inputs may further include at least one of the group of stimuli apparatuses that produce a visual stimulus, an audio stimulus, a scent stimulus, a temperature stimulus, or a tactile stimulus.

Immersion, as perceived by the user, increases as more senses are engaged. A single sensory stimulus is not as immersive as a multi-sensory experience. Multi-sensory experiences may be accomplished by choreographing two or more senses across time and space or by affecting a user's partition of motion or position relative to time. Creating an immersive experience may require control of the user's environment and sensory stimuli. The space of a vehicle cabin, especially the cabin of an autonomous vehicle provides a chamber in which a stimulus that is presented to the user or passengers can be fully controlled.

Orchestrating multiple sensory inputs or modalities may allow for new experiences or more powerful perceptual experiences. The five key or traditional senses are vision, hearing, smell, touch, and taste. However, humans have other senses beyond the traditional five senses, sometimes referred to as the "5+ Senses". They include proprioception (i.e. awareness of our body and position) cardioception (i.e. awareness of our heartbeat), echolocation (i.e. spatial awareness due to acoustic effects), thermoception (i.e. sensing temperature), time perception, agency perception (i.e. the subjective feeling of choice or perception of control).

An immersive experience employs a plurality of the above senses. Additionally, it is possible to connect the 5+ Senses (e.g. proprioception or time perception) to one or more of the five traditional senses (e.g. vision or hearing) in a multi-sensory experience. Using the "body ownership" concept allows for reinforcement or compounding of the multi-sensory experience by forging a believable immersion and perceived connection between the passenger's body and their subjective experience of their surroundings.

A body ownership experience reinforces a person's perceived physical and psychological connection with an experience. This is accomplished by sensory immersion that brings the person into the moment of the experience causing them to believe the experience in a way that is tangible or beneficial. The body ownership experience is also accomplished through the incorporation of biofeedback into specific sensory stimuli. In one example concerning the human sense of sight, a body ownership experience may contain the following core attributes:

The apparatus that produces visual stimuli may consist of a visual projector, such as a digital projector, AR or VR head mounted display.

Selectively bathing the user's or passenger's body in light or projected motion graphics. Selectively bathing the surrounding space, surfaces, or environment in light or projected motion graphics. Selectively combining both the body and surroundings (e.g. space, surfaces or environment) in light or projected motion graphics. Combining multi-sensory stimuli and inputs, choreographed with the illumination from light or projected motion graphics.

In an example concerning the sense of hearing, the user may experience audible rhythms that correspond to their or other passenger's biorhythms.

A biorhythm is any a recurring cycle in the physiology or functioning of a human, mammal, or another living organism. This may include vital signs (such as pulse rate, temperature, respiration rate, and blood pressure) as well as more prolonged rhythms such as such as the daily cycle of sleeping and waking. A biorhythm may be sensed or monitored by measurement or prediction of physiological rates or signals of a user (i.e. bio-signals). Multiple sensors may be used to monitor a user's biorhythms. In one example, physiological or biological rates (e.g. simple frequency information expressed as Hz, bpm, etc.) may be measured and reported as biorhythm information. In another example, physiological signals or bio-signals may be measured and detailed rates or information may be extracted from the measured physiological signals or bio-signals. The measured signals may be complex signals that can provide information on cycle stages and phases of a human body. For example, heartbeats or breathing may be sensed or measured by a sensor(s) and biorhythm information such as a pulse or heart rate (HR), heart rate variability (HRV), a respiration rate (RR), inhale-pause-exhale (IPE) timing, and respiratory sinus arrhythmia (RSA) may be extracted or reported to an analyzing unit.

Emotion recognition may be done using camera techniques such as facial gesture, blood flow, temperature, etc.). The user's emotional state could be an influencer to the rate of entrainment or target entrainment. Some specific modes such as meditation or relaxation might look for specific facial gestures states as part of a guided meditation or relaxation exercise (e.g. a neutral expression could be as important as a smile or frown).

The biorhythm may be determined by prediction, extrapolation, or interpolation of physiological rates or information. The prediction, extrapolation, or interpolation may be used if there are gaps in sensor data (e.g. due to limitations of the sensing technology, motion of the user, or interference from other signals) or where prediction, extrapolation, or interpolation may enhance the entrainment experience.

In an example concerning the sense of touch, the user may experience a haptic or surface touch (e.g. seat adjustment, massage or bolster features pulse in synchronization to the biorhythm) that reflects the characteristics of the passenger's (or other passenger's) biorhythms.

Body ownership and end-experience may include an entrainment experience that provides biofeedback of one or more physiological signals or biorhythms, to enhance immersion and perceived connection.

Body ownership experiences may be useful for emotional or mood control. They may provide a meditation and relaxation experience. They may be used for driver-vehicle safety-critical relationships, such as vehicle mode awareness (e.g. autonomous driving levels 2 and 3), or remedying distraction or inattention. They may be used for therapeutic experiences, such as remedying motion sickness or providing stress relief. They may also be used as part of scent-based functional (e.g. therapeutic) and aesthetic or hedonic experiences.

A body ownership system may sense, in real-time, the human body's physiological signals or biofeedback, the physical human body and body gestures, and the cabin surroundings (e.g. surfaces, objects or environment). Biofeedback may include the following biorhythms: breathing (respiration rate and or RSA), heart rate (or HRV), brain waves, or emotion. Additionally, the biorhythm may not come from the user but from another person or passenger to create biorhythm entrainment between two or more passengers.

The system further adapts the human sensory inputs and experience, according to the objectives of the experience (e.g. entrainment, mood control, meditation, mode awareness, scent based experiences, etc.). The system may utilize the five key human senses and the other 5+ senses. The system may adapt the surroundings (cabin surfaces, objects, or environment) in real-time. For example, this may include adjusting the seating and body support posture or adjusting the interior panels. Additionally, the physical motion of the human body may also be required to incorporate either to the touch sense or proprioception. Body position awareness typically requires motion to "calibrate" the awareness. The system may also include interactive elements that provide feedback and control of the experience. This may be presented through a graphical user interface, projected interface (projected onto the body or surrounding cabin surfaces or seats) or smart devices.

An experience such as driving or riding in a vehicle may be made up of many sub-experiences. Sub-experiences can be experiences, interactions or sensory stimuli that result from the various features and functions that are found in the car (e.g. driving, infotainment, navigation, seat, lighting, windows, etc.). These sub-experiences can relate to any occupant, modalities, timing, duration, scale, or position. These sub-experiences all add up to form an impression or perception of the overall experience. It is common in Experience Design practice to use brand design languages to coordinate sub-experiences. These are often centered on the visual experience and consequently touch on the other senses dependent on other relevant modalities (e.g. a sound and haptic relative to a touch-screen, touch, temperature, and smell relative to the color-material-finish of a seat, etc.).

Coordinating these sub-experiences may improve the holistic experience in a premium sense. Choreographing and coordinating these sub-experiences into a holistic experience may be accomplished by applying entrainment and biofeedback techniques. Using a common timeframe that is derived from the occupant's biorhythms (i.e. think of a common beat that everything marches or dances to). Using multi-sensory immersive approaches such as digital projection to create a perceivable (conscious or subconscious) connection between the human and the experience—to thereby reinforce an emotional connection with the experience and vehicle.

Using body ownership experiences in a vehicle may create an "empathic car," meaning a car where the occupant(s) feel(s) an emotional connection with the experiences, the vehicle and socially with the other occupants. Analogous to the rubber hand illusion, the empathic car creates the impression—either (consciously or subconsciously—that the vehicle experience is an extension of one's self (e.g. an extension of one's philosophical experience of being).

The one or more human sensory outputs may receive gesture information. The experience system may be further configured to alter the entrainment experience based on the gesture information. The use of gesture information may allow the experience to be better presented to the user. This may include allowing a user to control the experience with gestures. It may also include the system reading the conscious or subconscious gestures of the user and altering the entrainment experience with the gesture information. In an embodiment, using digital projection mapping and 3D tracking of the human body and surroundings may allow the creation of an augmented reality (AR) experience. In a simple example, the projection of motion graphics may communicate the user's current breathing rate. The user may then use hand gestures to control the entraining breathing rate (e.g. by setting a target breathing rate). Additionally, body position, posture and orientation may also be used (e.g. different targets may be triggered depending on if the user sits up, sits forwards, or lies down, etc.). Additionally, gestures may not only control the entrainment rhythm such as the breathing rate but may also change other experience dynamics such as by setting the mood or emotion of the motion graphics, lighting, or sound.

In another example, in an entrainment experience designed to reduce a driver's stress, a driver of a vehicle may have a moderately increased heart rate but one that is not determined conclusively to be high. Using gesture information, such as the wave of a user's hands, may signal to the system to administer the entrainment experience where biofeedback alone would not justify it alone.

The system may further include the experience system further configured to receive biorhythm information relating to a portion of the user's body, wherein providing the entrainment experience further comprises mapping the user's body with the visual input apparatus and projecting the entrainment experience at the portion of the user's body mapped by the visual input apparatus. Allowing the user to visualize the area of their body that relates to the biofeedback and the entrainment rhythm may increase the effectiveness of the experience. For example, by projecting an entrainment experience designed to entrain respiration rate on the user's chest the user may be better able to synchronize the entraining rhythm with their breathing. In this example, the projection moves with the user to deepen the user's connection with the experience.

Representing biofeedback by utilizing the user's own body as sensory input and output creates a type of AR. This may be done both using sensory input using the human body as a canvas via for projection mapping. And sensory output recognizing the body movement and gesture (e.g. facial, hand, body posture, gesture, motion, and position) via digital observation techniques.

The visual input apparatus may track and map a physical space of the user. Additionally, providing the entrainment experience may comprise projecting the entrainment experience to the physical space of the user. By projecting the entrainment experience around the user instead of directly on them, they may feel more immersed in the experience increasing the like hood of entrainment. Including the physical space of the user allows the user to focus on other things—such as driving a vehicle, having a conversation, or listening to music—while still entraining as the rhythm may still be in their peripheral vision. Further, by projecting the experience in the user's virtual space, other individuals that can witness the entrainment may find themselves also entrained. This could be useful if it is desired to synchronize the biorhythms of multiple people to one individual or user.

The one or more human sensory inputs may include a plurality of the group of stimuli apparatuses and determining the entrainment experience is further based on the plurality of stimuli apparatuses. The system may determine the entraining experience based on the human sensory inputs available to it. For instance, an entrainment experience would differ in a vehicle with a visual projector, an audio system, a seat massager, and access to temperature controls then if only a subset of those inputs were available.

According to another example, determining the entrainment experience may be further based on an experience setting. For example, in a vehicle and entrainment experience may differ depending on the mode of the car. If a car is in a sport setting an entrainment experience may look to excite the user by entraining their heart or breathing rate to increase. However, if the car is in a setting that encourages economic driving, the entrainment experience may be adjusted to encourage calm or passive driving. In this way, an entrainment experience using biofeedback may be used as a basis for other multi-sensory experiences offered by connected systems.

An experience setting may be determined programmatically. For instance, if a car is in autonomous driving mode but still requires an alert driver, the entrainment experience may be set to encourage the driver to remain alert. However, the experience setting may be determined by the user. For example, if they sought a sporty or exciting entrainment experience.

The entrainment experience may be provided either inside or outside a vehicle. The entrainment experience may be in a vehicle. Entraining a driver or passenger of a vehicle may improve the driving experience of the entrained individuals.

It may also improve the safety of the vehicle's operation by reducing human errors, such as by encouraging alertness through entrainment of the heart, lungs or brain.

Additionally, the entrainment experience is provided to the user with at least one of a smartphone, a tablet computer, a smartwatch, a wearable device worn by the user, virtual reality (VR), AR, or mixed reality (MR). This would allow entrainment to be introduced in environments without dedicated human sensory inputs.

Another example relates to a method for performing and providing an entrainment experience to a user. The method comprises communicating with one or more human sensory inputs and an entraining rhythm generation unit. The method further comprises receiving entraining rhythm information from the entraining rhythm generation unit, determining an entrainment experience based on the entraining rhythm information, and providing the entrainment experience to the user via the one or more human sensory inputs.

Further, the method might be stored on a non-transitory machine-readable medium storing instructions that, when executed by a computer, provide an entrainment experience to a user. Providing an entrainment experience communicating with one or more human sensory inputs and an entraining rhythm generation unit. The method further comprises receiving entraining rhythm information from the entraining rhythm generation unit, determining an entrainment experience based on the entraining rhythm information, and providing the entrainment experience to the user via the one or more human sensory inputs. Using a non-transitory machine-readable medium allows the entrainment experience to be performed on computer-controlled entrainment systems. This means that the entrainment experience can be added to systems with an update to systems that previously could not perform the method.

BRIEF DESCRIPTION OF THE DRAWINGS

Some embodiments of apparatuses and systems will be described in the following only by way of example and with reference to the accompanying figures, in which.

DETAILED DESCRIPTION

Various embodiments will now be described more fully with reference to the accompanying drawings in which some embodiments are illustrated. The thicknesses of lines, layers, and/or regions in the figures may be exaggerated for clarity.

Accordingly, while further embodiments are capable of various modifications and alternative forms, some particular embodiments thereof are shown in the figures and will subsequently be described in detail. However, this detailed description does not limit further embodiments to the particular forms described. Further embodiments may cover all modifications, equivalents, and alternatives falling within the scope of the disclosure. Same or like numbers refer to like or similar elements throughout the description of the figures, which may be implemented identically or in modified form when compared to one another while providing for the same or similar functionality.

It will be understood that when an element is referred to as being "connected" or "coupled" to another element, the elements may be directly connected or coupled via one or more intervening elements. If two elements A and B are combined using an "or", this is to be understood to disclose all possible combinations (i.e. only A, only B, as well as A and B) if not explicitly or implicitly defined otherwise. An alternative wording for the same combinations is "at least one of A and B" or "A and/or B". The same applies, mutatis mutandis, for combinations of more than two elements.

The terminology used herein to describe particular embodiments is not intended to be limiting for further embodiments. Whenever a singular form such as "a," "an" and "the" is used, and using only a single element is neither explicitly nor implicitly defined as being mandatory, further embodiments may also use plural elements to implement the same functionality. Likewise, when functionality is subsequently described as being implemented using multiple elements, further embodiments may implement the same functionality using a single element or processing entity. It will be further understood that the terms "comprises," "comprising," "includes" and/or "including," when used specify the presence of the stated features, integers, steps, operations, processes, acts, elements, and/or components but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the embodiments belong.

Figure 1:
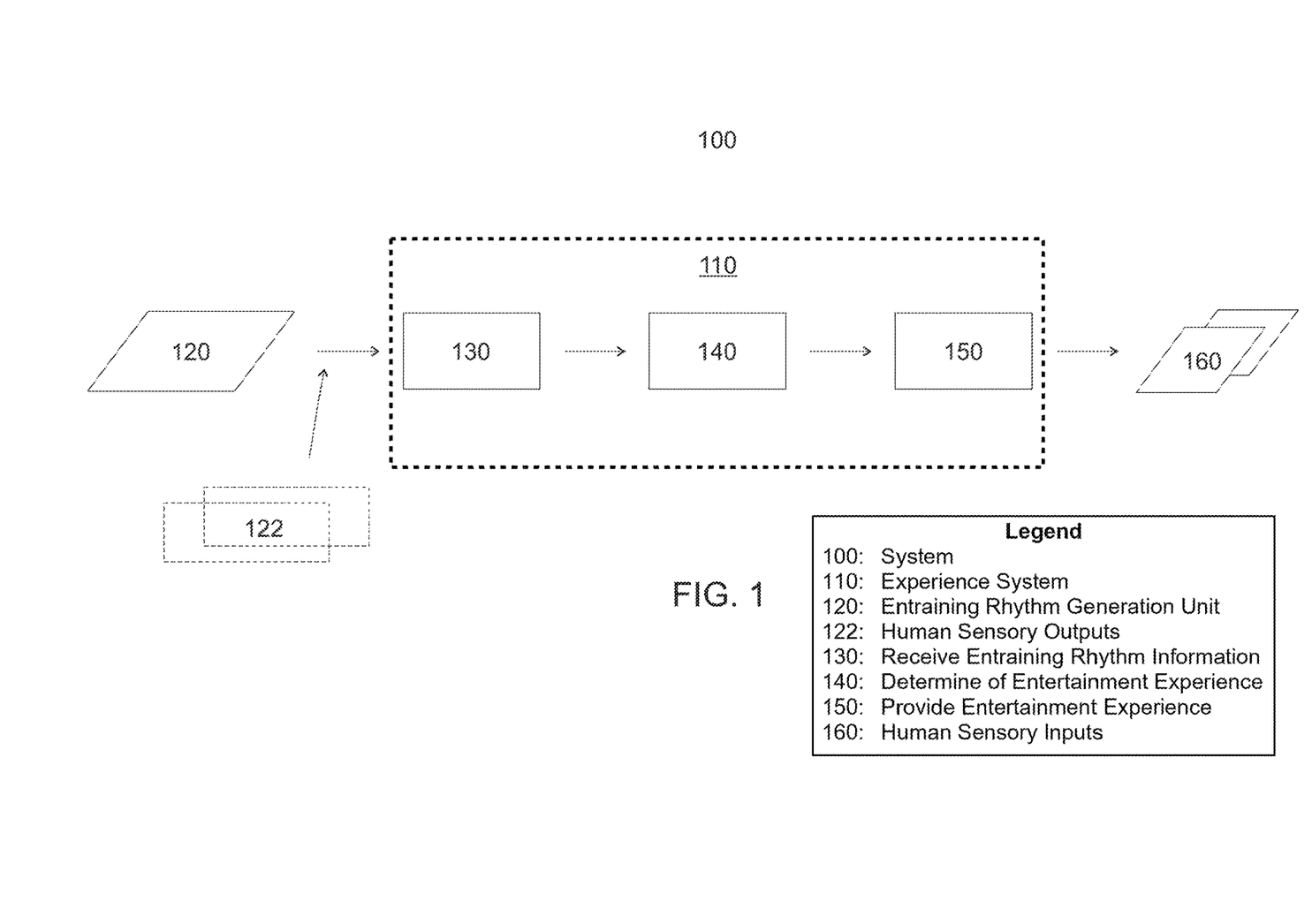
FIG. 1 shows a block diagram of an embodiment of a system for providing an entrainment experience to a user.

FIG. 1 shows a system 100 for providing an entrainment experience to a user, the system comprising an experience system 110 in communication with one or more human sensory inputs 160 and an entraining rhythm generation unit 120. The experience system 110 is configured to receive 130 entraining rhythm information from the entraining rhythm generation unit 120, determine 140 the entrainment experience based on the entraining rhythm information, and provide 150 the entrainment experience to the user via the one or more human sensory inputs 160.

The user may be any person with access to the system. The user may also be driver, a passenger, or another occupant of a vehicle. For example, in a fully autonomous vehicle, the entrainment experience may be provided 150 to one or more users.

The entraining rhythm generation unit 120 generates an entraining rhythm based on the entraining target for providing an entrainment experience to the user, and control one or more human sensory inputs to the user based on the entraining rhythm. Entrainment is provided or experienced when a human body adapts in some way to some rhythm from an external source. Entrainment may be a voluntary or involuntary, conscious or sub-conscious. The entrainment may happen internally to the human body or be exhibited externally (e.g. brain waves, breathing, toe-tapping, etc.). The sensation of entrainment can be "actual entrainment" (e.g. some extent of physiological synchronization) or "perceived entrainment" (e.g. similar to a placebo effect). It is not important whether the user experiences theoretical entrainment but feels a sensation and has a perceived benefit.

The entraining rhythm generation unit 120 may be configured to generate an entraining rhythm based on the entraining target for providing an entrainment experience to the user, and control one or more human sensory inputs 160 to the user based on the entraining rhythm. The entraining rhythm controls the rhythm of all human multi-sensory inputs 160 in an environment, which may be inside or outside a vehicle. The entraining rhythm can be a pattern or time-based framework for synchronizing any sensory modalities, events, or experiences presented to the user. The entraining rhythm is used for providing biofeedback to the user to progressively adapt the user's biorhythm for the entrainment experience in a looping process (i.e. the user's biorhythm may be entrained in multiple steps with a biofeedback loop).

The entraining rhythm is used as a beat or timing to control one or more human sensory inputs 160 to the user. For example, the entraining rhythm generation unit 120 may generate the entraining rhythm that the experience system 110 then receives 130. The experience system 110 provides 150 information to control human sensory inputs 160. Human sensory inputs 160 may be one of lighting intensity or color, airflow, temperature, audio characteristics or musical content of an infotainment system, seat system, graphical features of a user interface, and the like. The experience system 110 may determine 130 an entrainment experience by controlling the time-related behavior, transitions, synchronization and operations of the experience. For instance, the audio characteristics (e.g. volume, fade, balance, spatial properties, etc.), as well as the musical content of the audio (e.g. rhythm, beat, tempo, melody, etc.) may be controlled by the entraining rhythm. The music may be procedurally generated or manipulated by a computer such that the music is in time/phase to the entraining rhythm. The vehicle seat system features that can be controlled by the entraining rhythm may include motion, position, orientation, fit or size, massage (e.g. haptic, vibrational or motion, such as delivered by pneumatic or electromechanical means), temperature, or ventilation.

Human sensory inputs 160 are any biofeedback devices that can indicate, represent or demonstrate biorhythm characteristics to a human. An input can be a device that demonstrates comparison between entrainment target rate and actual rate (biofeedback rate), the rate or frequency of a biorhythm, detailed physiological pattern or activity (e.g. for respiration: Inhale-Pause-Exhale cycle), motion (e.g. of the lungs, chest, heart, etc.), or any device that uses that human body and its surroundings as a canvas to impart information.

Biosignals of a user may be sensed by a sensors 130 and provided to the analyzing unit 110. A biorhythm is any rhythm (any repetitive sequence or pattern) that occurs in the human body. For example, the biorhythm may be a breathing rate of the user, a heart rate of the user, brain waves of the user, circadian rhythm of the user, body rhythm (any repetitive movement, behavior, or motion of a body or body parts) of the user, emotion of the user, etc.

In some examples, a user state (i.e. a biorhythm of a user, such as a breathing rate or heart rate) may be predicted or estimated by analyzing the historical data. The estimation or prediction of the user state may be made based on the last known or received data. For example, the running average calculated over a period of time may be used in estimating or predicting the user state. Alternatively, more complex mathematical interpolation may be used.

Alternatively, a user state (i.e. a biorhythm of a user, such as a breathing rate or heart rate) may be predicted or estimated based on relationships with other bio-signal data from sensors. For example, a breathing rate of a user may be estimated from heart-related data (such as photoplethysmography (PPG) data, electrocardiography (ECG) data, or the like). The PPG or ECG data may be provided by on-board sensors on wearable devices such as smartwatches and their apps.

In a hybrid approach, the historical data may be combined (factored) with any available other biosensor data in estimating the state of the user.

In some examples, the biorhythm may be self-reported rates or targets by a user. For example, the biorhythm may be reported by the user based on experience or aspirational goals of the user. The user may input a numerical value for a biorhythm (e.g. a breathing rate) or choose a mode or level (e.g. relaxation or meditation level) or type of experience, for example, via a graphical user interface. Alternatively, a smart system may provide recommendation(s) or options for the user to choose and the user may choose one of the recommendations or options.

The physiological/biological signals may be sensed and gathered directly by sensors or devices installed in a vehicle. The sensors and devices may be integrated with a vehicle. Alternatively or additionally, the physiological/biological signals may be sensed and gathered by an external device(s) including sensor(s). For example, the external device(s) may be a user device 140 e.g. mobile devices, such as smartphones, smartwatches, wearable sensor(s) and software apps (on the devices or in the cloud), etc.

One example of biorhythm sensed by a sensor is a breathing rate (respiration rate). The breathing rate/respiration rate is the number of breaths a person takes per minute. The breathing rate may be a total respiration cycle (i.e. breaths per minute), a respiration cycle without pauses (or without significant pauses), a respiration cycle with pauses (inhale, pause (intra-pause), exhale, and pause between cycles (inter-pause)), or an RSA. Generally, sensors can provide average or instantaneous respiration rates. It is also possible to detect inhalation and exhalation phases of breathing (e.g. using a camera, a strain gauge (i.e. for sensing chest expansion/motion), microphone or radar sensing techniques).

Respiration control may be voluntary or involuntary. Respiration is a unique physiological process that is normally an unconscious, involuntary and autonomous physiological process. Yet the human can over-ride the autonomous control and control it entirely voluntarily, deciding when to breathe and how deeply. With the right entrainment conditions, it may be possible for respiration control to be less conscious and more subconscious. For example, in a similar way to how a couple of people walking together, may walk in synchronization without consciously being aware of or intentionally walking in step.

Other examples of biorhythm sensed by a sensor(s) include a heart rate or heart rate variability (HRV). Smartwatches or other wearable devices may use PPG or ECG sensors for monitoring a heart rate or HRV data. PPG is a technique for measuring the variation in the absorption of light by human skin. PPG has been used for heart rate measurement. ECG is a test that measures the electrical activity of the heartbeat. Remote photo-plethysmography (RPPG) is a camera-based method to estimate a heart rate and HRV. RPPG is used for measuring cardiac pulse rates from live or recorded video. A vehicle may include a driver-facing camera in a vehicle cabin and this driver-facing camera may be used to detect heart-related biorhythm using the RPPG. In some examples, the stress levels of a user may be estimated from the HRV data. An application(s)

running on smartwatches, smartphones, or any user device may gather and share the data (e.g. directly or via a network (cloud)).

Other examples of biorhythm sensed by a sensor(s) include brain waves (e.g. brain signals such as alpha waves). Brain waves are oscillating electrical voltages in the human brain. Alpha waves are one type of brain waves. Sensing brain waves may require a head-mounted wearable device. Alternatively, sensors may be placed in the headrest of a vehicle seat.

Biorhythm sensed by a sensor(s) may include circadian rhythms (e.g. sleep or napping patterns). There are relationships between biorhythms (such as respiration and heart rates) and sleep patterns. Sleep, naps, and jetlag may be considered as rhythmic experiences that can be designed in the context of a vehicle cabin. In one example, breathing control and entrainment may create relaxation that also appears to induce sleepiness.

Research shows that naps should not be longer than around 15 minutes to avoid sleep inertia (a "grogginess" that is a physiological state of impaired cognitive and sensory-motor performance that comes after sleep, especially broken sleep). A breathing rate in non-rapid eye movement (REM) sleep becomes lower and more regular than during REM sleep and when awake. During REM sleep, eyes move quickly in different directions. It does not happen during non-REM sleep. A sleep pattern of a user may be self-reported or estimated from physical behaviors such as motion and eye closure and bio-signals such as heart rate.

Biorhythms sensed by a sensor(s) may include body rhythms. Body rhythms are repetitive and externalized movements, behaviors, or motions of a body or body parts, such as walking, swaying, dancing, finger or foot tapping, etc. These behaviors and body motions may be considered as an externalized indication of entrainment to an internal rhythm (e.g. spontaneous beat) or external rhythm (e.g. any entrainment experience, music). Research has shown that humans use spontaneous behavioral synchrony (e.g. dancing, tapping, etc.) when they intend to make affiliative and social relationships (as a means to connect individuals with others).

In one example, cameras and microphones combined with machine learning may be used to detect rhythmic physical activity. It can also look for how rhythmic activity is coordinated with music. By monitoring or looking out for this activity, the level of immersion, engagement or affinity in an experience may be measured, especially if there is an obvious beat to the entraining rhythm (e.g. audio, music, lighting, or the like).

Biorhythms sensed by a sensor may include blinking. Blinking may be measured with the use of a camera. Blinking is correlated with stress, fatigue, and drowsiness (reduction in blink rate and increased eye closure). Research has shown that blinking and eye closure can be used to disengage attention (e.g. to focus one's thoughts), and blinking correlates with medical conditions such as Parkinson's disease and Tourette's syndrome.

Biorhythm sensed by a sensor(s) may include emotion. Emotion is not a time-based physiological rhythm, but emotions can have patterns, driven by context and may be indirectly related to time and routine. Emotion may be sensed or monitored by a camera and a relevant algorithm by detecting facial expressions, gestures, etc. For example, the indications of emotions (e.g. a smile for happiness/joy or brow furrow for anger, etc.) may be sensed, for example, with a camera. The time-based metrics (e.g. patterns, rates, averages, etc.) may be monitored for emotions and those metrics may be used to drive or influence the experience or aspects of the sensory experience.

The one or more human sensory inputs 160 of the system 100 may include at least one of the group of stimuli apparatuses that produce: a visual stimulus, an audio stimulus, a scent stimulus, a temperature stimulus, or a tactile stimulus. The apparatus that produces visual stimuli may consist of a visual projector (such as a digital projector, AR or VR head-mounted display).

Stimuli apparatuses or devices may illuminate through a graphical display, light, and video projection. For example, the lighting and video projection on a user's body and surroundings can shift color, increase or decrease in size, fade on and off, sweep up, down, or radially. The motion graphics or lighting effects may be centered on the chest, area of the lungs or mouth to communicate breathing. The motion graphics or lighting may radiate out from the body to illuminate the seating and surroundings. Illumination effects may be achieved by blending colors or graphics from different illumination sources (e.g. LEDs, video projectors, etc.) that might relate to the boundary (e.g. junction or shadow) between the subject's body and seat or surroundings. Other human sensory inputs 160 may be an interactive user interface via a graphical display, projected interface (onto the body or surrounding surfaces or seats) or smart device (e.g. smartphone or smartwatch). Other human sensory inputs 160 may relate to audio feedback (such as sound effects that are discrete or progressive to communicate aspects of the biorhythm characteristics), smell (such as the use of scent and fragrance to reinforce the experience), temperature, and tactile feedback from the cabin surroundings, surfaces, space, and environment (such as the seating and body support). An example of a human sensory input 160 that provides tactile feedback is the control of the conventional massage components in a seat.

The entraining rhythm information received 130 by the experience system 110 may comprise at least one of a master rhythm determined based on biorhythm information, a slave rhythm determined based on the master rhythm, or an arbitrary rhythm.

The entraining rhythm generated by received 130 by the experience system 110 may be a master (i.e. primary) rhythm determined based on biorhythm information. Alternatively, the entraining rhythm may be a slave (i.e. secondary) rhythm determined based on the master rhythm (e.g. where the slave rhythm has a phase relationship (e.g. defined using a mathematics or physics wave definition) to the master relationship). Alternatively, the entraining rhythm may be an arbitrary rhythm (e.g. determined by a fixed timing, e.g. based on research test or anecdotal data). The master rhythm may be generated based on a single data input or source (i.e. a single sensor or device) or an aggregation of multiple data inputs or sources (i.e. multiple sensors or devices). Different slave rhythms may be generated for different human sensory inputs 160, sensory modalities, different systems, or devices that deliver the sensory input(s) or experience to the user.

As an example, a case of entrainment of a breathing rate will be explained. It should be noted that the examples disclosed herein apply to entrainment of any biorhythm other than a breathing rate entrainment. A breathing rate of a user may be monitored with a sensor/camera. The mode (objective) may be set to a relaxation mode, which aims to provide relaxation for the user. Scientific research has shown that a breathing rate in the range of 5, 6, or 7 breaths per minute (bpm) optimizes relaxation. This is the entrainment goal in this example, i.e. the target that can provide or increase relaxation.

A normal breathing rate of a person is around 20 bpm, which may increase with physical activity and stress. The stress may be work-related, life-related, or arise from instantaneous situations such as driving. For instance, when driving in a traffic jam, bad weather, or with an impending deadline such as when a user is late for an important appointment. In such situations, the current breathing rate of the user is monitored and the entraining rhythm generation unit 120 generates an entraining rhythm to provide relaxation for the user. The entraining rhythm is generated based on an entraining target for each entraining period. The system 100, receives 130 the entraining rhythm information, determines how to deliver 140 the entraining rhythm, and then provides 150 the entraining rhythm to the user via the human sensory inputs 160. The breathing rate of the user is progressively entrained until it reaches 5, 6, or 7 bpm. For example, the entraining target may be initially set at 18 or 16 bpm. When the user shows signs of reducing their breathing rate to a range close to the entraining target, it may be incrementally reduced by 2 to 4 bpm. This process is repeated until the user reaches the final entrainment goal (e.g. 5, 6 or 7 bpm). The entraining rhythm is used as a beat or timing to control one or more human sensory inputs to the user. One or more human sensory inputs 160 are controlled based on the entraining rhythm to progressively decrease the breathing rate over a period of time (e.g. 2-3 minutes, 5 minutes, 10 minutes, or any periods of time) using biofeedback provided by the human sensory inputs 160. This is done until the user's breathing rate reaches the goal (e.g. 5, 6, or 7 bpm).

FIG. 1 further shows that the experience system 110 of the system 100 may be in communication with one or more human sensory outputs 122, wherein the one or more human sensory outputs 122 track the user and wherein providing the entrainment experience comprises projecting the entrainment experience at the user. Additionally, the one or more human sensory outputs 160 of the system 100 may receive gesture information and the experience system 110 may be further configured to alter the entrainment experience based on the gesture information.

Incorporating gesture information into the system 110 may reinforce the user experience and user immersion, by making the experience reactive and responsive to any user input (e.g. body, hand, facial, and posture, gesture, movement, activity, position, etc.). The recognition would work in tandem with the projection mapping, a system combining both sensory input and output. Gesture input may be obtained from a user as touch gesture recognition relative to a user interface (e.g. capacitive display). A user interface may have manual controls to control the rate of entrainment or characteristics of the system or experience (e.g. the time to progressively reach the entrainment target), direction of entrainment (lower or higher). This may allow the user to manually select a particular function or mode (e.g. relaxation, sport, mood, driving mode, etc.).

Other gestures may include, mid-air gesture recognition (e.g. hand and body). This may be camera-based, with or without projection mapping. When an entrainment experience is projected onto the body (e.g. hand, arm, torso, body parts or whole-body) the user's mid-air gesture recognition may allow the user to manually control the functions, features, or modes. For example, raising or lowering a hand or finger gesture might increase or lower the entrainment rate, or change aspects around the mode, mood, etc. (e.g. changing the lighting color from a calm color to an energetic color).

Additionally, the body position or gestures of the user may also effects the entrainment. For example, tracking the digital projection to the body to create a type of AR so that the digital projection follows with the body movements (both projection onto the body and surrounding vehicle cabin area). The system 110 recognizes that the user's body (and body parts) posture, position and motion (e.g. lying down, sitting up, sitting forwards, etc.), or transitioning between different positions or states. The system 110 can set up an experience that is relevant to the body position. For example, a user lying down may be perceived by the system 110 as more calm and oriented towards resting and sleep. This could be also be contextually informed by the status of features such as the infotainment system (e.g. watching a movie, listening to music, reading a book, vs. napping/sleeping). Additionally, leaning forwards may imply interest and attention. Sitting up may be neutral or depend on other contextual clues or cues. If combined with body projection, the motion graphics that are projected on the body can become interactive, such that the motion graphics appear to respond to the motion of the body, whilst also communicating the entrainment rhythm. Other gestures may include if the user's body is moving rhythmically (e.g. toe or finger tapping, head bobbing, etc.) or in time to music.

The system 100 may run intelligently so as to look at data to minimize the level of interaction or input required from the user.

Human sensory inputs 160 and outputs 122 may relate to proprioception and body motion. A user's body gesture and position can affect, control, or drive entrainment experience as well as the method of human sensory input 160, specifically with respect to illumination (e.g. lighting, graphical display or projection). For example, a motion graphics "halo" may be projected onto the passenger or their surroundings which responds to both their physical behavior.

The system 100 may be adapted for multiple users. For example, to portray or visualize the differences in biorhythms. In this example, lighting or projected motion graphics may create visual effects that surround the passenger and the visual effects may interact, dance, move or merge according to the rate, rhythm, and motion of the passenger's biorhythms or physical behavior.

The system 100 may also be adapted to show the relationship between different biorhythms or physiological signals as well as the relationship with other factors internal or external to the vehicle (e.g. the passage of time, the status of the vehicle, etc.).

The experience system 110 presents the entrainment experiences to the user via human sensory inputs 160 that can be single, multi-modal, or multi-sensory inputs, stimuli or experiences. The entrainment experience may be provided within a vehicle or outside of a vehicle (in another location, such as at home). The entrainment experience may be delivered by a device(s) or a system(s) in a vehicle cabin, such as a climate control system (e.g. an air conditioner, a heater, etc.), an infotainment system, seating features (e.g. a seat massage, a seat heater or cooler, etc.), lighting, user interfaces, interior surfaces such as shades, interior panels, windows, moon/sun-roofs, etc. For example, the vehicle seat system (e.g. with features including position, motion, articulation, massage, temperature, airflow, etc.) embedded in a vehicle seat may be controlled by the entraining rhythm for providing the entrainment experience. Alternatively, the entrainment experience may be delivered by external or third-party devices, including smartphones, smartwatches, smart-glasses, or any wearable devices, or through VR, AR, or MR. Entrainment experiences can be stronger when multiple senses are stimulated simultaneously.

The entrainment experiences by examples disclosed herein may provide functional, aesthetic, or emotional benefits, for example, relaxation and stress relief, alertness and attention to safety, moments of beauty, sensory reinforcement of existing use cases or experiences, etc.

The experience system determines 140 how the entraining rhythm controls the rhythm of all human multi-sensory inputs inside or outside a vehicle. The entraining rhythm can be a pattern or time-based framework for synchronizing any sensory modalities, events, or experiences presented to the user. The entraining rhythm represents a target rhythm for entraining user. The entraining rhythm may comprise a number of elements. For example, the experience system 110 may control at least one of lighting intensity or color, airflow, temperature, audio characteristics of an infotainment system, seat system features, and graphical features of a user interface in a vehicle based on the entraining rhythm.

The entraining rhythm is used as a beat or timing to control one or more human sensory inputs 160 to the user. For example, lighting pulses may be generated in intensity or color in synchronization with the entraining rhythm (e.g. 6 bpm). The airflow may be controlled to fluctuate from high to low, or low to high, in synchronization with the entraining rhythm. The temperature may be controlled to fluctuate in time (or in a scaled phase relationship) to the entraining rhythm. The infotainment audio volume may be adjusted (e.g. from medium to high, etc.) by the entraining rhythm. The seat massage features may be activated, deactivated, or changed in time to the entraining rhythm. The user interface in a vehicle may be adjusted such that a graphical or motion graphics of the user interface may pulse with the entraining rhythm, and provide feedback on the status of the entrainment experience and the difference between the entrainment target (e.g. a breathing rate target) and the entraining rhythm (e.g. a current breathing rate).

Figure 2:
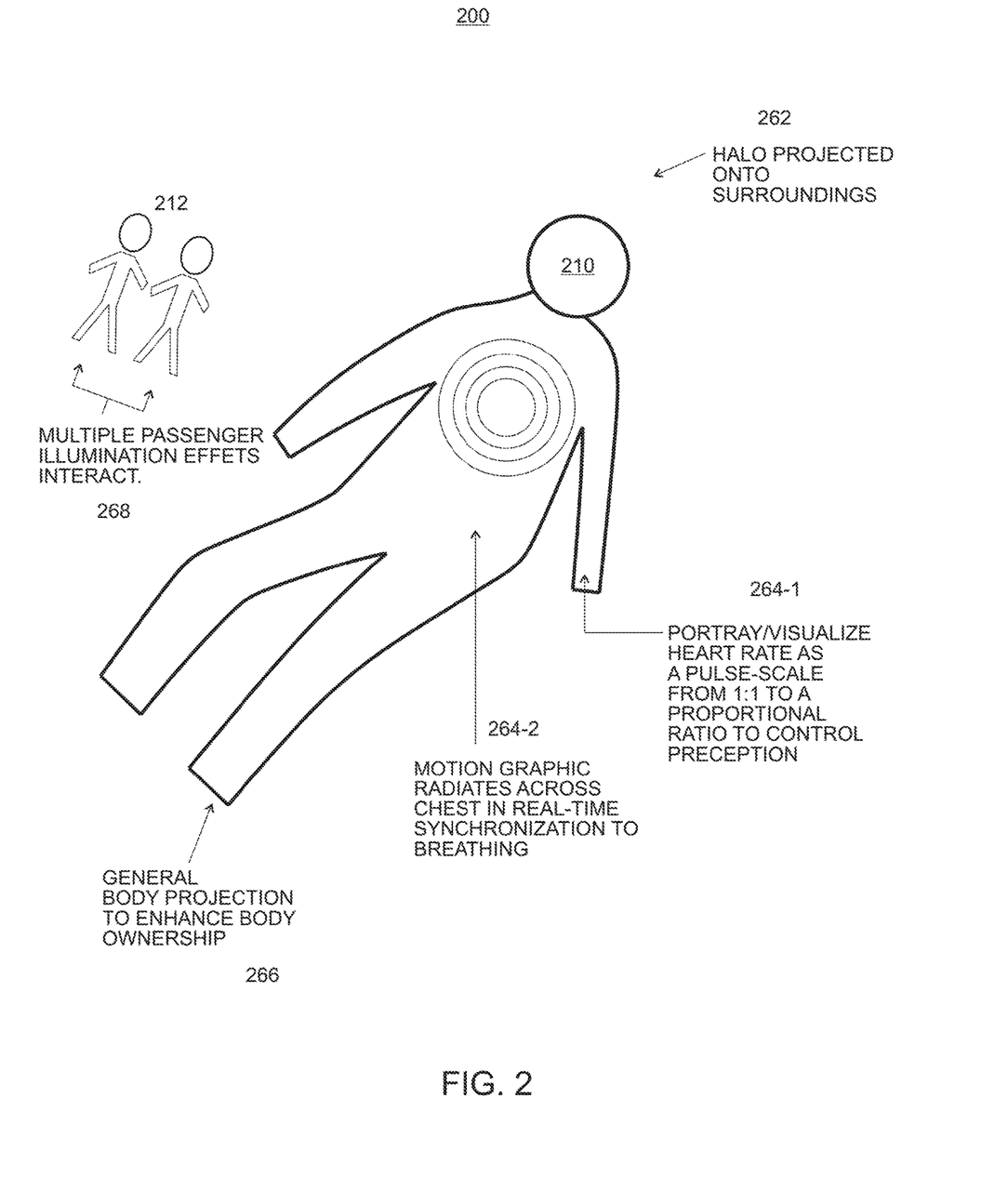
FIG. 2 shows an embodiment of the system where the human sensory input is a visual projector.

FIG. 2 shows the system 200 further configured to receive biorhythm information relating to a portion of the user's body 210, wherein providing the entrainment experience further comprises mapping the user's body 210 with the visual input apparatus and projecting the entrainment experience at the portion 264 of the user's body 210 mapped by the visual input apparatus. For example, the visual input apparatus may be projected at a user's arm 264-1 to portray or visualize a heart rate as a pulse. The system 200 may show an accurate representation of the pulse beating at the user's wrist or my scale to a wider area, such as the entire arm, to control the user's perception of the entraining rhythm. Likewise, motion graphics could radiate across the chest 264-2 in real-time synchronization to the breathing. Further, the visual input apparatus may also do general body projection 266 to highlight the user's body 210 and enhance body ownership. By doing general projection it may be made more obvious to the user that an entrainment rhythm is being targeted to a certain portion 264 of the body when the general projection 266 changes to a specific one 264.

FIG. 2 further shows the system 200, wherein the visual input apparatus tracks and maps a physical space of the user and providing the entrainment experience comprises projecting the entrainment experience to the physical space of the user. The visual input apparatus may project the entrainment experience as a halo 262 around the user or on their surroundings. Additionally, if there are multiple users 212 the illumination effects of the multiple users 212 may interact 268 as their individual halos 262 collide.

Figure 3:
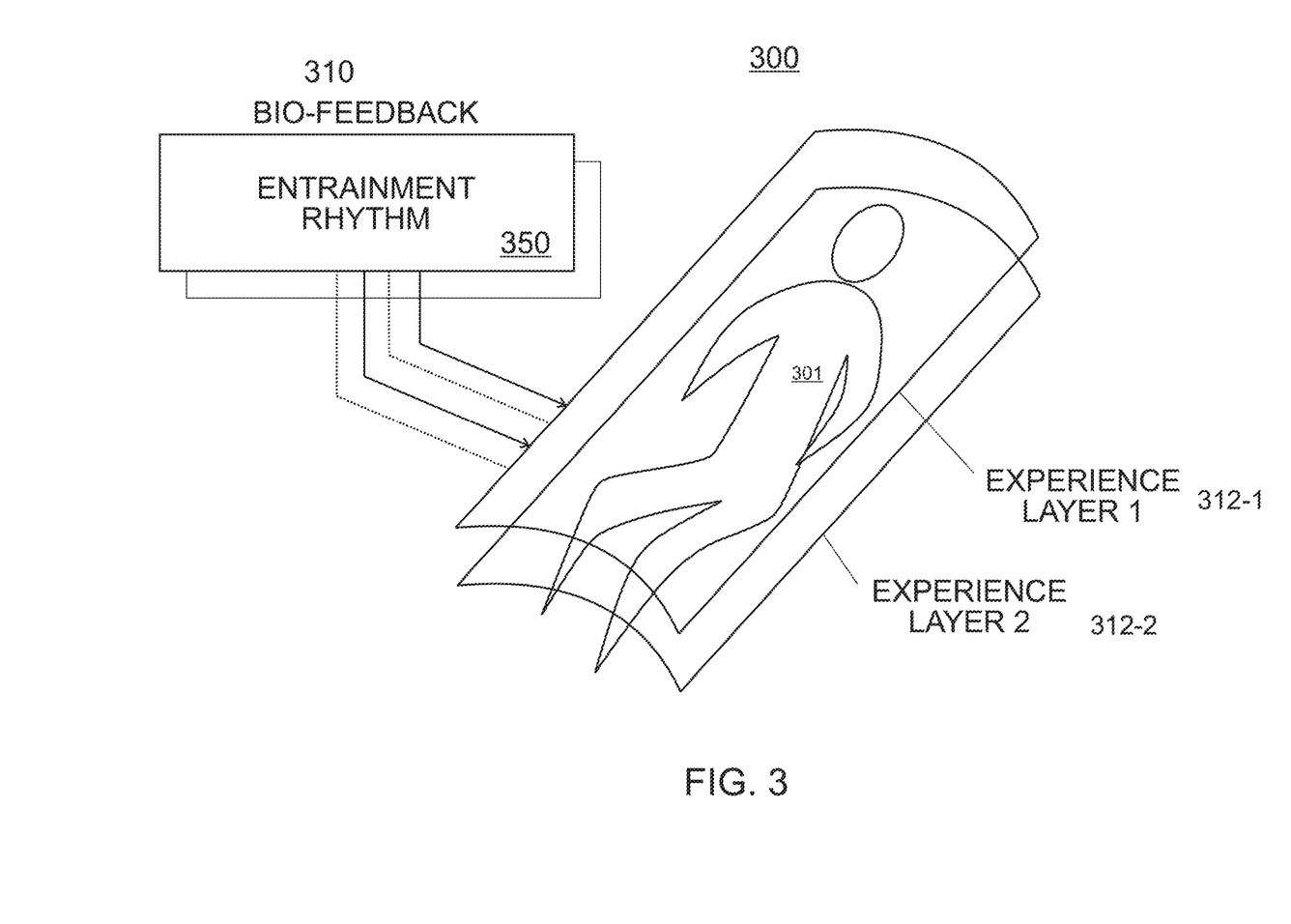
FIG. 3 shows an embodiment of the method wherein the entrainment experience incorporates a plurality of experience layers.

FIG. 3 shows the system 300 wherein one or more human sensory inputs include a plurality of the group of stimuli apparatuses 350 and determining the entrainment experience is further based on the plurality of stimuli apparatuses. The entrainment experience may be further based on an experience setting and that experience setting may be determined by the user 301. Each entrainment experience may be delivered or perceived by the user 301 as a layer 312. With multiple layers 312-1, 312-2 pertaining to different stimuli apparatuses or a single stimuli apparatus delivering multiple feedback rhythms. For example, a visual input apparatus may project a plurality of entrainment experiences as halos or layers 312 around the user 301 with a first halo 312-1 pertaining to a heart beat entrainment rhythm and a second or further layer pertaining to a breathing rate. These entrainment layers 312 may augment the reality that the user 301 experiences and immerse the user 301 or users in an entrainment experience.

The system entrainment experience may be provided either inside or outside a vehicle. A vehicle may be any type of land-, sea-, and air-based vehicle or transportation system. Providing 150 the entrainment experience can be done through any apparatus that employs this system. The provision can be done using an integrated, onboard human sensory input system included in the vehicle or by an independent system located within the vehicle's cabin. Additionally, the system is vehicle independent and may be deployed in environments and systems not used or designed for transportation, such as in a home, a retail environment, public spaces, an office or any of the climate systems that operate in those spaces.

The entrainment experience may be provided to the user with a user device, such as a smartphone, a tablet computer, a smartwatch, a wearable device worn by the user, a device implementing VR, AR, or MR, or the like. VR is a simulated experience that can be similar to or completely different from the real world. AR is an interactive experience of a real-world environment where the objects that reside in the real world are enhanced by computer-generated perceptual information across multiple human sensory modalities, including visual, auditory, haptic, somatosensory, and olfactory. MR is merging of real and virtual worlds to produce new environments and visualizations.

Figure 4:
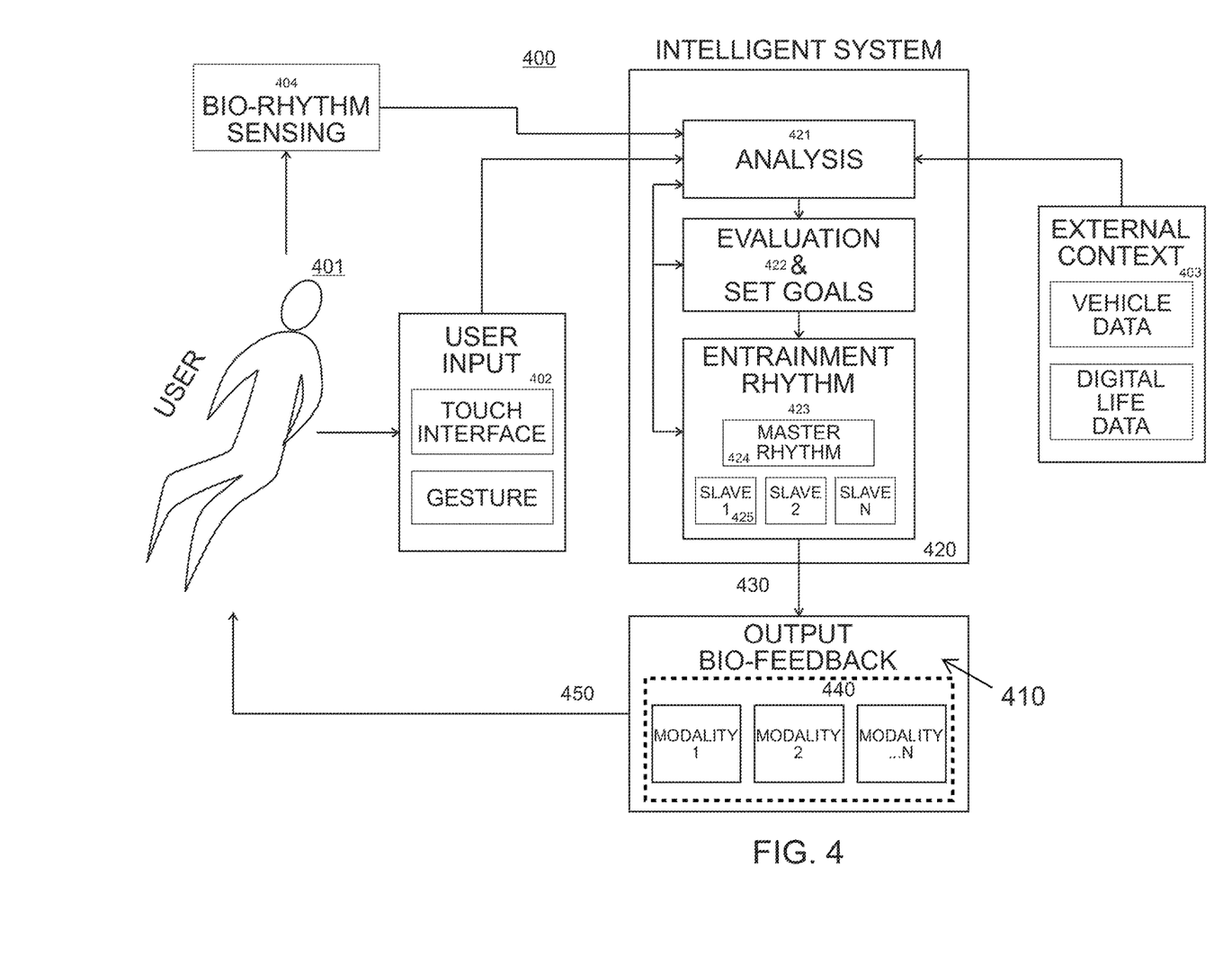
FIG. 4 shows a system for entraining a user that incorporates the system for providing an entrainment experience to a user.

FIG. 4 shows the experience system 410 as part of a larger entrainment system 400. The experience system 210 is in communication with one or more human sensory inputs 404 and an entraining rhythm generation unit 420. The experience system 410 is configured to receive 430 entraining rhythm information from the entraining rhythm generation unit 420, determine 440 the entrainment experience based on the entraining rhythm information, and provide 450 the entrainment experience to the user via the one or more human sensory inputs. The system 400 may be in communication with one or more human sensory outputs 402, 404 and further configured to receive feedback information from the one or more human sensory outputs 402, 404 and provide the feedback information to the entraining rhythm generation unit 420. The system 400 may also be in communication with external context systems 403 that may provide external data, such as vehicle data or digital life data to the entraining rhythm generation unit 420.

Figure 5:
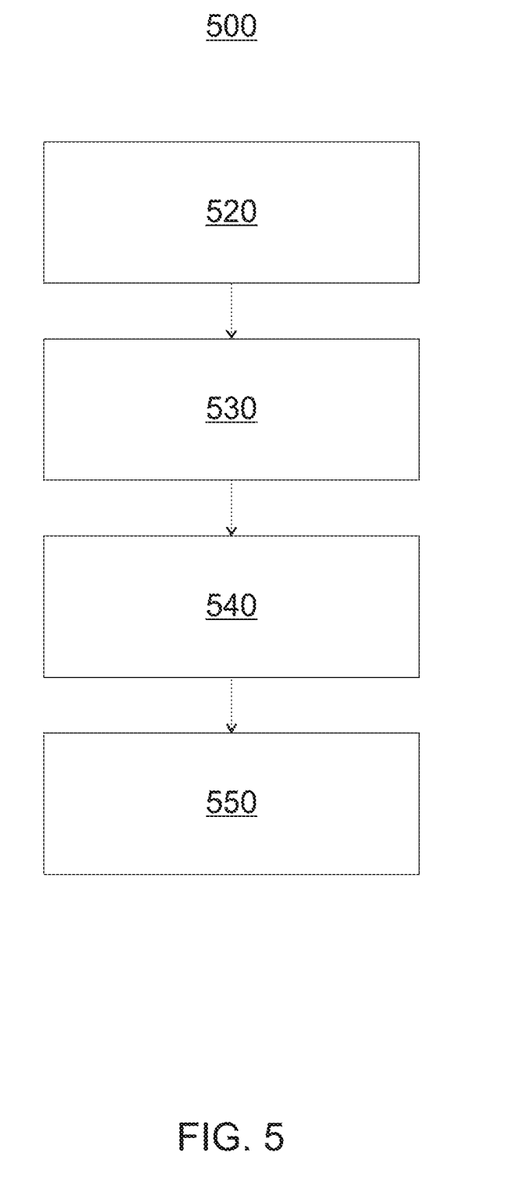
FIG. 5 shows block diagram of an embodiment of a method for performing for providing an entrainment experience to a user.

FIG. 5 shows a method 500 for performing for providing an entrainment experience to a user. The method comprises communicating 520 with one or more human sensory inputs and an entraining rhythm generation unit. The method further comprises receiving 530 entraining rhythm information from the entraining rhythm generation unit, determining 540 an entrainment experience based on the entraining rhythm information, and providing 550 the entrainment experience to the user via the one or more human sensory inputs.

Additionally, the method might be performed by a program stored on a non-transitory machine-readable medium storing instructions that, when executed by a computer, provide an entrainment experience to a user. Providing an entrainment experience communicating with one or more human sensory inputs and an entraining rhythm generation unit. The method further comprises receiving entraining rhythm information from the entraining rhythm generation unit, determining an entrainment experience based on the entraining rhythm information, and providing the entrainment experience to the user via the one or more human sensory inputs. Using a non-transitory machine-readable medium allows the entrainment experience to be performed on computer-controlled entrainment systems. This means that the entrainment experience can be added to systems with an update to systems that previously could not perform the method.

Any of the above-described embodiments may be combined with any other embodiment (or combination of examples) unless explicitly stated otherwise. The foregoing description of one or more implementations provides illustration and description but is not intended to be exhaustive or to limit the scope of embodiments to the precise form disclosed. Modifications and variations are possible in light of the above teachings or may be acquired from practice of various embodiments.

The aspects and features mentioned and described together with one or more of the previously detailed embodiments and figures, may as well be combined with one or more of the other examples to replace a like feature of the other embodiment or to additionally introduce the feature to the other embodiment.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor, or computer-readable and encode machine-executable, processor-executable, or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further embodiments may also cover computers, processors or control units programmed to perform the acts of the above-described methods or (field) programmable logic arrays ((F)PLAs) or (field) programmable gate arrays ((F)PGAs), programmed to perform the acts of the above-described methods.

The description and drawings merely illustrate the principles of the disclosure. Furthermore, all examples and embodiments recited herein are principally intended expressly to be only for illustrative purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof.

A functional block denoted as "means for . . . " performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the figures, including any functional blocks labeled as "means", "means for providing a signal", "means for generating a signal.", may be implemented in the form of dedicated hardware, such as "a signal provider", "a signal processing unit", "a processor", "a controller", as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software but may include digital signal processor (DSP) hardware, network processor, application specific integrated circuit (ASIC), FPGA, read only memory (ROM) for storing software, random access memory (RAM), and non-volatile storage. Other hardware, conventional or custom, may also be included.

A block diagram may, for instance, illustrate a high-level circuit diagram implementing the principles of the disclosure. Similarly, a flow chart, a flow diagram, a state transition diagram, a pseudo code, and the like may represent various processes, operations, or steps, which may, for instance, be substantially represented in computer-readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims might not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples/embodiments a single act, function, process, operation or step may include or may be broken into multiple sub-acts, -functions, -processes, -operations, or—steps, respectively. Such sub acts may be included and part of the disclosure of this single act unless explicitly excluded.

Furthermore, the following claims are hereby incorporated into the detailed description, where each claim may stand on its own as a separate example/embodiment. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

What is claimed is:

1. A system for providing an entrainment experience to a user in a physical space, the system comprising:
    an experience system comprising a processor, the processor configured to communicate with an entraining rhythm generation unit and one or more human sensory inputs comprising at least a visual projector,
        wherein each of the one or more human sensory inputs deliver a sensory stimulus to the user,
        wherein the sensory stimulus delivered by the visual projector is illumination of a body of the user,
    the processor further configured to:
        receive entraining rhythm information from the entraining rhythm generation unit,
            wherein the entraining rhythm information comprises a master rhythm based on biorhythm information received from the user or a slave rhythm based on altering the master rhythm,
            wherein the biorhythm information relates to at least the user's lungs or heart, determine the entrainment experience by altering the delivery of the sensory stimulus to provide a representation of the master or slave rhythm, and provide the entrainment experience to the user and the physical space around the user via the one or more human sensory inputs, wherein the visual projector illuminates the user's body and radiates illumination from the user's body into the physical space adjacent to the user's body.

2. The system of claim 1 wherein the experience system is in communication with one or more human sensory outputs, the experience system further configured to receive feedback information from the one or more human sensory outputs and provide the feedback information to the entraining rhythm generation unit.

3. The system of claim 1 wherein the entraining rhythm information comprises at least one of a second master rhythm or a second slave rhythm, wherein the second master and slave rhythms are based on a second biorhythm information,
    wherein determining the entrainment experience comprises altering the delivery of the sensory stimulus to provide a representation of the second master or slave rhythm.

4. The system of claim 1 where the one or more human sensory inputs further includes at least one of the group of stimuli apparatuses that delivers to the user:
    a visual stimulus,
    an audio stimulus,
    a scent stimulus,
    a temperature stimulus or
    a tactile stimulus.

5. The system of claim 1 wherein altering the delivery of the sensory stimulus of the visual projector to provide a representation of the master or slave rhythm comprises fading the illumination of the visual projection according to the master or slave rhythm.

6. The system of claim 1 wherein the experience system is in communication with one or more human sensory outputs, wherein the one or more human sensory outputs track the user and wherein providing the entrainment experience comprises projecting the entrainment experience at the user with the visual projector.

7. The system of claim 6 wherein the one or more human sensory outputs receives gesture information and the experience system is further configured to, alter the entrainment experience based on the gesture information.

8. The system of claim 6 wherein
    the experience system is further configured to receive biorhythm information relating to a portion of the user's body, wherein providing the entrainment experience further comprises mapping the user's body with a projection mapping apparatus and projecting the entrainment experience at the portion of the user's body mapped by the projection mapping apparatus with the visual projector.

9. The system of claim 6 wherein one or more human sensory outputs is a projection mapping apparatus,
    wherein the projection mapping apparatus collects tracking and mapping information from the physical space of the user and
    providing the entrainment experience comprises projecting the entrainment experience to the physical space of the user using the tracking and mapping information.

10. The system of claim 4 wherein the one or more human sensory inputs include a plurality of the group of stimuli apparatuses and determining the entrainment experience is further based on the plurality of stimuli apparatuses.

11. The system of claim 1 wherein determining the entrainment experience is further based on an experience setting.

12. The system of claim 11 wherein the experience setting is determined by the user.

13. The system of claim 1 wherein the entrainment experience is provided either inside or outside a vehicle.

14. The system of claim 1 wherein the entrainment experience is provided to the user with at least one of a smartphone, a tablet computer, a smartwatch, a wearable device worn by the user, virtual reality, augmented reality, or mixed reality.

15. A method for providing an entrainment experience to a user in a physical space using an experience system comprising a processor, the method comprising:
    receiving entraining rhythm information from an entraining rhythm generation unit, wherein the entraining rhythm information comprises a master rhythm based on biorhythm information received from the user or a slave rhythm based on altering the master rhythm,
        wherein the biorhythm information relates to at least the user's lungs or heart, determining the experience by altering the delivery of a sensory stimulus, wherein the sensory stimulus provides a representation of the master or slave rhythm,
        wherein one or more human sensory inputs, at least comprising a visual projector, delivers a sensory stimulus to the user,
        wherein the sensory stimulus delivered by the visual projector is illumination of a body of the user, and
    providing the entrainment experience to the user and the physical space via the one or more human sensory inputs, wherein the visual projector illuminates the user's body and radiates illumination from the user's body into the physical space adjacent to the user's body.

16. A non-transitory machine-readable medium storing instructions that, when executed by a processor, performs the method of claim 15.

17. A system for providing a visual entrainment experience to a user in a vehicle interior, the system comprising:
    an experience system comprising a processor, the processor configured to communicate with a visual projector and an entraining rhythm generation unit, the processor further configured to:
receive entraining rhythm information from the entraining rhythm generation unit,
wherein the entraining rhythm information comprises a master rhythm based on biorhythm information from the user or a slave rhythm based on altering the master rhythm,
wherein the biorhythm information relates to at lease the user's lungs or heart,
determine the entrainment experience by altering a projection of the visual projector to produce a representation of the master rhythm or slave rhythm and project the entrainment experience via the visual projector, wherein the visual projector illuminates a body of the user and radiates illumination from the user's body into the vehicle interior adjacent to the user's body.

18. The system of claim 1, wherein the biorhythm information comprises at least one of a group of the user's:
pulse or heart rate,
heart rate variability,
respiration rate,
inhale-pause-exhale timing, or
respiratory sinus arrhythmia.

19. The system of claim 17, wherein the biorhythm information comprises at least one of a group of the user's:
pulse or heart rate,
heart rate variability,
respiration rate,
inhale-pause-exhale timing, or
respiratory sinus arrhythmia.

20. The system of claim 17, wherein the processor is further configured to:
communicate with a seat of user in the vehicle, wherein the seat comprises an at least one feature for controlling the seat's position, vibration, temperature, or ventilation, determine the entrainment experience by altering the at least one feature of the seat to produce a representation of the master rhythm or slave rhythm, and
provide the entrainment experience by controlling the at least one feature of the seat.

\* \* \* \* \*